(12) United States Patent
Lepaysan et al.

(10) Patent No.: US 9,354,315 B2
(45) Date of Patent: May 31, 2016

(54) DEVICE FOR MEASURING WIND SPEED

(75) Inventors: Christophe Lepaysan, Toulouse (FR);
Raphaël Teysseyre, Toulouse (FR)

(73) Assignee: EPSILINE, Toulouse (FR)

( * ) Notice: Subject to any disclaimer, the term of this patent is extended or adjusted under 35 U.S.C. 154(b) by 0 days.

(21) Appl. No.: 13/499,619

(22) PCT Filed: Oct. 11, 2010

(86) PCT No.: PCT/FR2010/052149
§ 371 (c)(1),
(2), (4) Date: Jun. 13, 2012

(87) PCT Pub. No.: WO2011/042678
PCT Pub. Date: Apr. 14, 2011

(65) Prior Publication Data
US 2012/0242976 A1 Sep. 27, 2012

(30) Foreign Application Priority Data
Oct. 9, 2009 (FR) ..................................... 09 57080

(51) Int. Cl.
*G01P 3/36* (2006.01)
*G01S 17/58* (2006.01)
*G01P 5/26* (2006.01)
(52) U.S. Cl.
CPC .. *G01S 17/58* (2013.01); *G01P 5/26* (2013.01)
(58) Field of Classification Search
CPC ......... G01S 17/58; G01S 7/4916; G01P 5/26; G01P 3/36

USPC ................ 356/28, 28.5, 3.01–3.15, 4.01–4.1, 356/5.01–5.15, 6–22
See application file for complete search history.

(56) References Cited

U.S. PATENT DOCUMENTS 3,984,685 A * 10/1976 Fletcher et al. .......... 250/339.11
4,664,513 A    5/1987 Webb et al.
(Continued)

FOREIGN PATENT DOCUMENTS

DE    102007052795 A1    5/2009
FR       2720839 A1    12/1995
(Continued)

OTHER PUBLICATIONS

Scaluse et al. "Self-Mixing Laser Diode Velocimetry: Application to Vibration and Velocity Measurement", IEEE, 2004.*
(Continued)

*Primary Examiner* — Luke Ratcliffe
*Assistant Examiner* — Assres H Woldemaryam
(74) *Attorney, Agent, or Firm* — Seed IP Law Group PLLC

(57) ABSTRACT

A device comprises: an emitting element for emitting a laser beam, referred to as an emitted beam; a focusing element for focusing the emitted beam at a predetermined focal distance (D); a receiving element for receiving the emitted beam after being reflected by a particle in the air (18), referred to as a reflected beam; a transmitting element for transmitting the signal of interference occurring between the emitted beam and the reflected beam to a signal processor in order to deduce the speed of the particle therefrom. The emitting element includes a laser diode and the receiving element is combined with the laser diode by self-mixing. The focal distance is between 5 cm and 2 m.

11 Claims, 1 Drawing Sheet

(56) References Cited

U.S. PATENT DOCUMENTS

Figure 1:
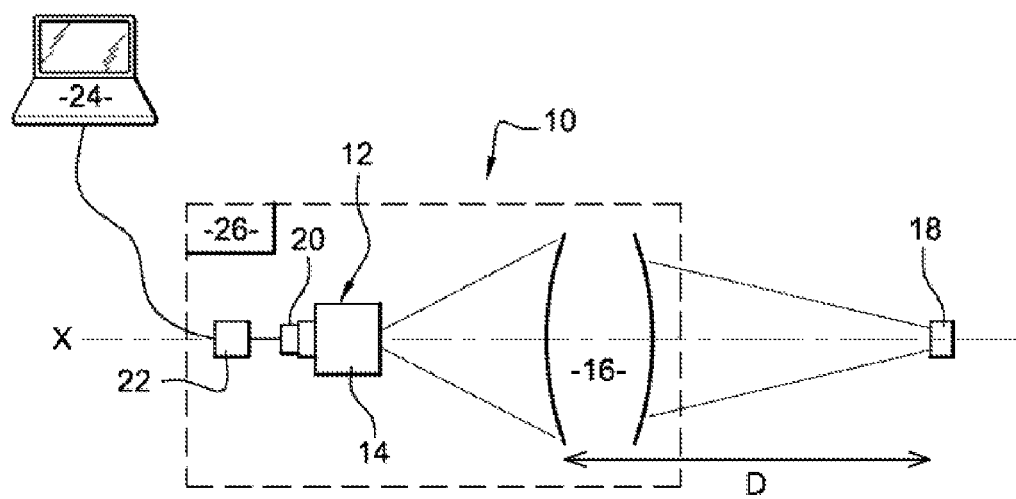

| | | | |
|---|---|---|---|
| 4,733,609 A * | 3/1988 | Goodwin et al. | 102/213 |
| 5,005,144 A | 4/1991 | Nakajima et al. | |
| 5,053,630 A * | 10/1991 | Hausamann et al. | 250/574 |
| 5,123,730 A * | 6/1992 | Holmes et al. | 356/28.5 |
| 5,594,543 A * | 1/1997 | de Groot et al. | 356/5.09 |
| 5,701,172 A * | 12/1997 | Azzazy | 356/28 |
| 6,100,516 A * | 8/2000 | Nerin et al. | 250/206.2 |
| 6,100,965 A * | 8/2000 | Nerin | 356/5.09 |
| 6,141,086 A * | 10/2000 | Vahala et al. | 356/28.5 |
| 6,320,272 B1 | 11/2001 | Lading et al. | |
| 6,759,671 B2 * | 7/2004 | Liess et al. | 250/559.32 |
| 6,885,438 B2 * | 4/2005 | Deines | 356/28.5 |
| 7,061,592 B2 * | 6/2006 | Deines | 356/28.5 |
| 7,068,355 B2 * | 6/2006 | Vahala et al. | 356/28 |
| 7,106,447 B2 * | 9/2006 | Hays | 356/450 |
| 7,202,942 B2 * | 4/2007 | Deines | 356/28.5 |
| 7,206,064 B2 * | 4/2007 | Rogers et al. | 356/28 |
| 7,423,736 B2 * | 9/2008 | Baillon et al. | 356/28 |
| 7,495,774 B2 * | 2/2009 | Hays et al. | 356/519 |
| 7,505,145 B2 * | 3/2009 | Hays et al. | 356/519 |
| 7,508,528 B2 * | 3/2009 | Hays et al. | 356/519 |
| 7,518,736 B2 * | 4/2009 | Hays et al. | 356/519 |
| 7,522,291 B2 * | 4/2009 | Hays et al. | 356/519 |
| 7,777,866 B1 * | 8/2010 | Kyrazis | 356/28.5 |
| 8,427,649 B2 * | 4/2013 | Hays et al. | 356/450 |
| 8,434,358 B2 * | 5/2013 | Asahara et al. | 73/170.02 |
| 2003/0016365 A1 * | 1/2003 | Liess et al. | 356/498 |
| 2003/0151732 A1 * | 8/2003 | Rogers et al. | 356/28.5 |
| 2007/0064219 A1 * | 3/2007 | Rogers et al. | 356/28 |
| 2007/0165130 A1 * | 7/2007 | Cobben et al. | 348/335 |
| 2007/0171397 A1 * | 7/2007 | Halldorsson et al. | 356/28.5 |
| 2007/0206180 A1 * | 9/2007 | Liess | 356/28 |
| 2008/0192229 A1 * | 8/2008 | Bruekers et al. | 356/28 |
| 2010/0277714 A1 * | 11/2010 | Pedersen et al. | 356/28 |
| 2010/0328680 A1 * | 12/2010 | Moench et al. | 356/615 |

FOREIGN PATENT DOCUMENTS

| | | |
|---|---|---|
| WO | 0029854 A1 | 5/2000 |
| WO | 2009046717 A2 | 4/2009 |
| WO | WO 2009/046717 * | 4/2009 |

OTHER PUBLICATIONS

Giuliani, G. et al., "Laser diode self-mixing technique for sensing applications," J. Opt. A: Pure Appl. Opt. (4):S283-S294, Nov. 1, 2002.

Wang, W.M. et al., "Self-Mixing Interference Inside a Single-Mode Diode Laser for Optical Sensing Applications," Journal of Lightwave Technology 12(9):1577-1586, 1994.

* cited by examiner

DEVICE FOR MEASURING WIND SPEED

The invention relates to the field of wind measurement, particularly when using laser light.

A prior art anemometer using a LIDAR (Light Detection And Ranging) system is known, particularly from document WO 2009/046717. This device emits a laser beam, focused by an optical system at a focal distance of several dozen meters, targeting a measurement volume in which particles in the air are blown about by the wind. These particles reflect the light received, emitting a beam in the direction of the optical system, referred to as the reflected beam. The LIDAR receives the beam reflected by the particles, and then processes the interference occurring between the emitted beam and the reflected beam in order to deduce the speed of the particles, as the frequency shift between the emitted beam and the reflected beam is dependent on this speed due to the Doppler effect.

Such a device for emitting laser beams is particularly costly to make.

One aim of the invention is to propose a wind speed measurement device that is less costly.

For this purpose, an object of the invention is a wind speed measurement device, comprising:
- a means for emitting a laser beam, referred to as the emitted beam,
- a means for focusing the emitted beam at a predetermined focal distance,
- a means for receiving the emitted beam after it is reflected by a particle in the air, referred to as the reflected beam,
- a means for transmitting the signal for the interference occurring between the emitted beam and the reflected beam to a signal processing means, in order to deduce the speed of the particle, wherein the emitting means comprises a laser diode and the receiving means is associated with the laser diode by self-mixing, the focal distance being between 5 cm (centimeters) and 2 m (meters).

By using a laser diode, a much more economical device for measuring the wind speed is obtained. In addition, the receiving of the reflected beam is achieved by self-mixing, which is particularly attractive. Self-mixing is also known as intracavity optical feedback, and corresponds to a device in which the reflected beam re-enters the same cavity as the beam emitted by the laser diode. Generally, the means for receiving the reflected beam comprises a photodiode, arranged just behind the laser diode, and the interference is created directly inside the laser cavity then received by the photodiode. The receiving means associated with the laser diode by the self-mixing provides optical amplification of the interference signal. The use of self-mixing is advantageous, because a laser diode and a photodiode are inexpensive, and they do not require a separate detector placed in a location other than that of the laser and receiving only the reflected beam after this reflected beam has been redirected by an interferometer. A photodiode placed just behind the diode is therefore used, and there is no need for management of the alignment issues related to an interferometer. The device is also particularly compact, because the reflected beam returns to the cavity of the laser diode. This is very different from the case of an interferometer which reflects the received beam, for example at an angle of 90° relative to the emitted beam, which requires placing the detector at a certain distance from the laser and therefore takes up space. Thus the proposed device can have the approximate volume of a cube with 1 cm edges, and of a cube with 10 to 20 cm edges if the signal processing means is included in the device, while a device equipped with a LIDAR generally has the approximate volume of a cube with 50 cm edges and weighs about 50 kg (kilograms).

One will note that the particles reflecting the light from the device are particles located in the air, often called airborne particles. These particles generally have a diameter of between 0.1 µm (micrometers) and 10 µm. The scattering occurring when the emitted beam is reflected is Mie scattering, which applies at the particle scale, in contrast to Rayleigh scattering which applies at the molecular scale. The particles can, for example, be particles containing carbon or ions.

The density of these particles in the air is very low and it is therefore difficult to obtain a continuous signal for analyzing the interference. Generally, the longer the focal distance, the better the measurement, because the presence of the device has little effect on the air movement.

Also, while anemometers comprising a laser generally focus at a distance of several dozen meters, the inventor had the idea of focusing at a shorter distance and observed that, for a focal distance of between 5 cm and 2 m, a sufficiently periodic signal of sufficient intensity is obtained for processing in order to provide the wind speed. Note that this signal is occasional, however.

By providing a focal distance of between 5 cm and 2 m, an appropriate use of the self-mixing phenomenon to measure the wind speed is made. By focusing at a shorter distance, more light is collected after it is reflected by the particle. Thus the power of the received signal can be greater than that generated by the noise from the laser diode and the device yields satisfactory results. Also, a focal distance greater than 5 cm is used so that air movement in the focus area is not affected by the presence of the device.

Note that the means of focusing the emitted beam focuses the towards a predetermined focus volume. This volume is sufficiently large for a signal to be reflected by one or more particles at least every few seconds, and sufficiently small for the light from the laser beam to be sufficiently concentrated. The device is adapted to process a beam reflected by particles having a diameter of between 0.1 and 10 µm, for example a particle containing carbon or an ion.

The device may additionally comprise one of more of the following features.

The signal transmission means is electronic. It comprises a transmission board containing a printed circuit onto which electronic components are welded, in order to act as an interface between the receiving means of the device and the signal processing means. Note that this transmission board is configured in a specific manner, to be able to transmit a processable signal for the interference occurring between the emitted beam and the reflected beam. In particular, the board is configured to emit relatively low noise, given that the signal reflected by the particles is intermittent and relatively weak.

The signal transmission means comprises an electronic amplification means, to provide electronic amplification of the interference signal. This amplification is particularly useful because the signal is intermittent and relatively weak.

The laser diode is a diode emitting in single longitudinal mode. The signal is therefore easier to process than when the diode has a higher power and is multimode. The laser diode can be a Fabry-Perot diode, for example.

The signal processing means is configured to select a portion of the received signal, namely the portion having an amplitude or power exceeding a threshold corresponding to the amplitude or power of a signal obtained by measuring in a windless location. It is particularly useful to select only a portion of the received signal. The interference signal generated by a particle is occasional and it is therefore advantageous to select only the portion of the signal that has a certain amplitude or power, corresponding to the actual interference. Instead of using the entire received signal with no pre-selection, we propose processing only the portion of the signal corresponding to a peak and only deducing the wind speed from that portion. One will note that it is possible for the selection by the signal processing means to occur after pre-processing the received signal. For example, a Fourier transform can first be applied to the received signal, then the selection can be made on the signal resulting from this transform. Such a selection can consist of selecting the portion of the transform having an amplitude or power greater than a threshold corresponding to the amplitude or power of the Fourier transform of a signal obtained when measuring in a windless location.

The signal processing means comprises a means for detecting a peak, a means for recording the signal within an interval of time around this peak, and a means for applying a Fourier transform to this signal. As the signal is occasional, applying a Fourier transform to the entire signal is more difficult to implement. By only applying the transform to a given portion of the signal, the results are particularly satisfactory for determining the wind speed.

The time interval during which the signal is recorded is between 50 and 300 μs (microseconds) around the peak.

The Fourier transform is done over a range of frequencies of between 0 and 1 GHz.

The wavelength of the light emitted by the laser diode is about 780 nm (nanometers). Other wavelengths can be considered, however.

The power of the laser diode is between 0 and 50 mW (milliwatts), preferably between 0 and 30 mW.

The Fourier transform is done over an interval of time of less than 200 μs (microseconds).

The device is powered by photovoltaic energy. The above device requires little energy, only a few watts (W), and therefore a photovoltaic cell can be used to operate this device, for example a cell providing 10 W of power. This is a particularly attractive type of power source, as the anemometer is placed outside and therefore has access to solar energy, and there is no need to install cabling to supply energy to the device. Note that the power source is not necessarily part of the device. Also, the device may be powered by other means, such as a battery for example.

The signal processing means is capable of providing the number of particles in the air, in addition to the particle speed. The amount of air pollution can be quantified in this manner, for example.

The device comprises three laser diodes, arranged in a manner that emits three non-coplanar laser beams. A very precise measurement of the wind speed in three dimensions is thus obtained, due to the fact that each laser diode allows obtaining the wind component in one direction, and the three directions are not coplanar. In other words, as a laser diode allows measuring the speed in one direction, the wind speed can be measured in one direction (one diode), in a plane (two diodes), or in three dimensions (three diodes).

The device comprises the processing means for processing the signal from the interference occurring between the emitted beam and the reflected beam. In this case, the processing means is part of the device.

Another object of the invention is a wind speed measurement system, comprising the device described above and the processing means for processing the signal from the interference occurring between the emitted beam and the reflected beam. In this case, the processing means is at a distance from the device.

Figure 2:
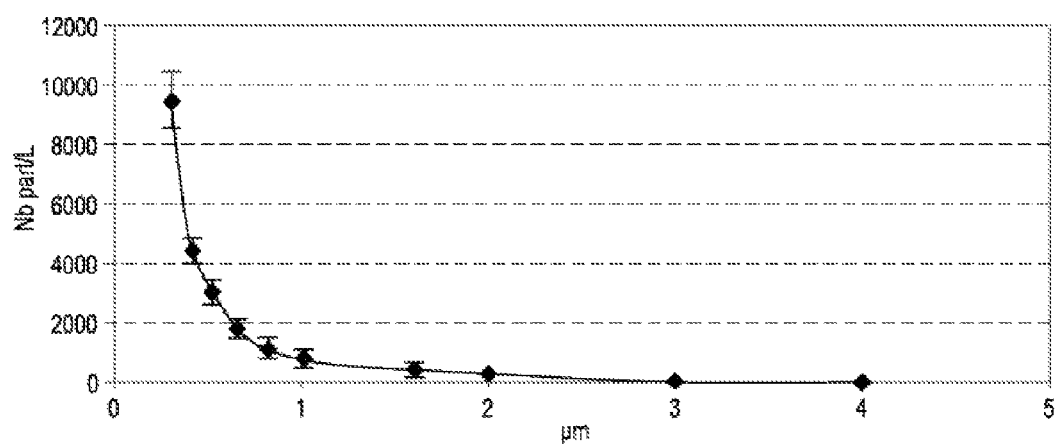

The invention will be better understood from reading the following description, provided solely as an example, with references to the attached drawings in which:

FIG. 1 is a schematic representation of an example of a wind speed measurement device; and FIG. 2 is a diagram illustrating an example of the particle size distribution for the air particles reflecting the laser light.

A wind speed measurement device 10 is represented in FIG. 1.

This device 10 comprises a laser beam emission means 12. The means 12 comprises a laser diode, for example a Fabry-Perot diode, emitting in single longitudinal mode, at a wavelength of 785 nm in this example. Other wavelengths can be used. In this example, the power of the laser diode 12 is between 0 and 30 mW. This laser diode 12 comprises an optical cavity 14 for amplifying the emitted laser light. The device 10 also comprises a focusing means 16, able to focus the beam emitted by the photodiode 12 towards a focus space 18. The focus volume 18, or effective volume, is at a distance D from the focusing means 16, this distance D corresponding to the focal distance of the device. The focal distance D is between 5 cm and 2 m.

The device 10 also comprises a means 20 for receiving a reflected beam. More specifically, this means 20 is configured to receive a beam emitted by the diode 12, after this beam is reflected by a particle in the air located in the focus volume 18, for example a particle composed of carbon or an ion. As can be seen in FIG. 2, the particle size in this example is in tenths of a μm, between 0.1 and 5 μm.

The receiving means 20 comprises a photodiode, arranged just behind the laser diode 12, and is associated with the laser diode 12 by self-mixing, meaning that the reflected beam travels back into the optical cavity 14 so that interference occurs between the emitted beam and the reflected beam.

The device 10 also comprises a transmission means 2 which transmits the interference signal to a processing means 24 for this signal, to enable deducing the speed of the particle or particles that reflected the emitted beam. The transmission means 22 is electronic. It comprises an electronic amplification means which amplifies the interference signal electronically. The transmission means consists for example of a transmission board, comprising a printed circuit onto which electronic components are welded, including operational amplifiers. The signal processing means 24 is configured to apply one or more Fourier transforms to the received signal in order to provide information concerning the wind speed. In this example, the means 24 is distanced from the device 10, but it could just as well be integrated with the device 10.

More specifically, the signal processing means 24 is configured to select a portion of the signal received by the transmission means 22, this portion corresponding to the portion of the signal having an amplitude or power greater than a predetermined threshold. This predetermined threshold corresponds to the amplitude or power of the signal received by the transmission means 22 after measuring in a windless location. In other words, this predetermined threshold is characteristic of the average noise of the device 10. This noise is then eliminated from the received signal when wind measurements are being calculated. The signal processing means 24 also comprises a peak detection means and a recording means for recording the received signal. This recording means is configured to record the signal over an interval of time around the detected peak. This time interval is between 50 and 300 µs around the peak, for example 90 µs, meaning that it starts 45 µs before the detected peak and stops 45 µs after the detected peak. In fact, a particle traveling into the beam produces a temporary sinusoidal signal of a duration determined by the interaction time between the particle and the beam. This duration is generally between 50 µs and 300 µs.

The signal processing means 24 comprises a means for applying one or more Fourier transforms to the recorded signal. The Fourier transform is done over a range of frequencies of between 0 and 1 GHz, for a time interval of less than 200 µs.

The signal processing means 24 is also capable, in this example, of providing the number of particles in the air, which allows deducing the air pollution in the vicinity of the focus volume 18.

The device 10 additionally comprises a power source 26, which may be in the form of a photovoltaic cell or any other type of power supply which allows the laser diode 12 to operate.

The operation of the device 10 will now be described.

In order to measure the wind speed, the laser diode 12 emits a beam, referred to as the emitted beam, which exits the cavity 14, travels into the optical system 16, and is then focused towards the focus volume 18. Air circulates in this focus volume 18, and therefore particles do as well. The focus volume 18 has sufficient dimensions to guarantee that at least one particle is inside this volume at intermittent times, for example at least every second, and is capable of reflecting the emitted laser beam. After reflection by at least one of the particles, the reflected beam travels back through the optical system 16, traverses the cavity 14, and is received by the photodiode 20. Interference can therefore occur, in the optical cavity 14, between the beam emitted by the diode 12 and the beam reflected by the particle. Also, the photodiode 20 receives an interference signal which is then transmitted to the processing means 24 by the transmission means 22. Note that the signal is electronically amplified before being transmitted to the processing means 24. The means 24 processes this received signal to deduce the speed of the particle or particles that reflected the beam. Because of the effect of the wind, a particle located within the volume 18 is moving relative to the receiver 20, so that the frequency of the reflected beam is shifted relative to the frequency of the emitted beam, due to the Doppler effect. Also, the frequency shift can be deduced from the interference signal, and therefore the component of the particle speed relative to the receiver 20 in direction X.

More specifically, using the interference signal, first a portion is selected by eliminating the portion of the received signal having an amplitude or power less than the threshold corresponding to the noise of the device 10, determined by measurement in a windless location. Then a peak is detected in the selected signal and the signal is recorded for an interval of time consisting for example of 45 µs before the peak to 45 µs after the peak. Next, one or more Fourier transforms are applied to this signal over an interval of time of less than 200 µs. The frequency shift between the emitted beam and the reflected beam can be deduced from this Fourier transform, and therefore the speed component in direction X.

This is a wind speed measurement device 10 which is inexpensive and requires very little space. In addition, the device 10 is easy to use because there is no need for alignment with an interferometer.

The invention is not limited to the embodiments described above.

In particular, in order to obtain better precision in the wind speed measurement, the device 10 can comprise three laser diodes 12, each emitting in a non-coplanar direction.

In the described example, the processing means 24 is placed at a distance from the device 10. However, the processing means 24 could easily be part of the device 10, for example as an electronic chip integrated with the device 10, configured to transmit information to a recorder that is remote from the device 10.

The invention claimed is:

1. A wind speed measurement device, comprising:
a first laser diode configured to emit a laser beam, referred to as the emitted beam,
focusing means for focusing the emitted beam at a predetermined focal distance between 5 centimeters and 2 meters,
receiving means for receiving a reflected beam produced by an air particle reflecting the emitted beam, the receiving means being associated with the first laser diode by self-mixing and configured to provide an interference signal corresponding to an interference occurring between the emitted beam and the reflected beam by the self-mixing;
a signal processing means configured to deduce a speed of the particle; and
transmission means for transmitting the interference signal to the signal processing means, the signal processing means being configured to:
select a first portion of the interference signal, the first portion having an amplitude or a power exceeding a threshold corresponding to an amplitude or a power of a signal obtained by a measurement in a windless location,
remove a second portion of the interference signal having an amplitude or a power that does not exceed the threshold corresponding to the amplitude or the power of the signal obtained by the measurement in the windless location, and
deduce the speed of the particle based on an analysis of only the first portion of the interference signal.

2. The wind speed measurement device according to claim 1, wherein the laser diode is a diode configured to emit in single longitudinal mode and not in a multimode.

3. The wind speed measurement device according to claim 1, wherein the signal processing means is configured to select the portion of the interference signal after prior processing of the interference signal.

4. The wind speed measurement device according to claim 1, wherein the transmission means is electronic and comprises a transmission board.

5. The wind speed measurement device according to claim 4, wherein the transmission means comprises electronic amplification means for amplifying the interference signal electronically.

6. The wind speed measurement device according to claim 1, wherein the signal processing means comprises detecting means for detecting a peak, recording means for recording the interference signal within an interval of time around the peak, and applying means for applying a Fourier transform to the interference signal.

7. The wind speed measurement device according to claim 6, wherein the time interval during which the interference signal is recorded is between 50 and 300 microseconds around the peak.

8. The wind speed measurement device according to claim 1, wherein the laser diode has a power between 0 and 50 milliwatts.

9. The wind speed measurement device according to claim 1, comprising a photovoltaic device configured to provide power based on photovoltaic energy.

10. The wind speed measurement device according to claim 1, comprising second and third laser diodes which are configured to emit, along with the first laser diode, three non-coplanar laser beams.

11. The wind speed measurement of claim 1, wherein the receiving means include:
- an optical cavity configured to receive the reflected beam and produce the interference by self-mixing the emitted beam with the reflected beam; and
- a photodiode to provide the interference signal corresponding to the interference produced by the self-mixing.

* * * * *